United States Patent
Parry et al.

[11] Patent Number: 5,973,326
[45] Date of Patent: Oct. 26, 1999

[54] GAS MONITORS

[75] Inventors: Michael Parry, Chelmsford; Alan Mason Doncaster, Maldon, both of United Kingdom

[73] Assignee: EEV Limited, Essex, United Kingdom

[21] Appl. No.: 08/906,090

[22] Filed: Aug. 5, 1997

[30] Foreign Application Priority Data

Aug. 10, 1996 [GB] United Kingdom .................. 9616809

[51] Int. Cl.⁶ .................................................. G01N 21/61
[52] U.S. Cl. ...................... 250/343; 250/341.8; 250/353; 250/373; 356/437
[58] Field of Search .................................. 250/343, 353, 250/341.8, 373; 356/437

[56] References Cited

U.S. PATENT DOCUMENTS

| | | | |
|---|---|---|---|
| 3,911,277 | 10/1975 | Cederstrand et al. | 250/343 |
| 3,921,158 | 11/1975 | Anderson . | |
| 4,266,219 | 5/1981 | Foster et al. . | |
| 4,657,397 | 4/1987 | Oehler et al. | 250/343 |
| 5,170,064 | 12/1992 | Howe . | |
| 5,440,127 | 8/1995 | Squyres | 250/341.8 |
| 5,550,375 | 8/1996 | Peters et al. . | |

FOREIGN PATENT DOCUMENTS

| | | |
|---|---|---|
| 0704691A2 | 12/1994 | European Pat. Off. . |
| 0704691 | 4/1996 | European Pat. Off. . |
| 3830906 | 9/1988 | Germany . |
| 1470381 | 4/1977 | United Kingdom . |
| 2245058 | 12/1991 | United Kingdom . |
| WO90/14581 | 11/1990 | WIPO . |
| WO91/05240 | 4/1991 | WIPO . |

*Primary Examiner*—Constantine Hannaher
*Attorney, Agent, or Firm*—Donald C. Casey

[57] ABSTRACT

A gas monitor includes an infra-red source enclosed within a housing having inner surfaces which are reflective. Radiation emitted from the source reflects off ellipsoidal surfaces and intermediate planar surfaces to be focussed at a sensor, being reflected five times. Radiation is absorbed by gas within the housing and a comparison of the source intensity and detected intensity gives a measure of the gas concentration. Use of ellipsoidal reflective surfaces directs emitted radiation along a plurality of routes having substantially the same path length, hence giving an accurate measure of the gas concentration with a compact device. In another embodiment, off axis parabolas are used to direct the radiation through the gas.

14 Claims, 3 Drawing Sheets

GAS MONITORS

FIELD OF THE INVENTION

This invention relates to gas monitors and more particularly to those in which optical radiation is transmitted through a gas and subsequently detected to provide information concerning the gas.

BACKGROUND TO THE INVENTION

In one known gas monitor, an infra-red source is arranged to emit radiation which passes through a gas to be monitored. Infra-red radiation is absorbed by the gas and that remaining is subsequently detected by a pyroelectric detector. A comparison is made between the source intensity and the intensity of radiation detected following passage through the gas to give the concentration of the gas. The concentration is related to the intensity by the following equation:

$$I = I_o e^{-\epsilon c l}$$

where I is the intensity of radiation detected by the detector, $I_o$ is the intensity of radiation emitted at the source, $\epsilon$ is effectively a constant which is dependent on the particular gas being monitored, c is the gas concentration and 1 is the distance travelled by the radiation through the gas.

In one known gas monitor, an infra-red source is located remote from a pyroelectric detector on a bench with a tube between them through which gas is passed. Infra-red radiation travels along a direct path between the source and sensor but there also tend to be multiple reflections from the interior surfaces of the tube. This results in numerous different path lengths taken by the infra-red radiation between the source and the sensor, which leads to errors in measuring the gas concentration. Moreover, the errors vary over time because the interior surfaces of the tube gradually degrade and present a non-uniform surface.

The present invention seeks to provide a gas monitor having improved characteristics over those previously known.

SUMMARY OF THE INVENTION

According to the invention, there is provided a gas monitor comprising an optical source, a sensor sensitive to light from the source, a chamber containing gas to be monitored and reflector means having reflective surfaces in the chamber, the source and sensor being substantially at foci of the reflector means and light being reflected at least three times before reaching the sensor from the source.

By using the invention, a plurality of folded optical paths are defined between the source and sensor through gas to be monitored, and the paths may be made substantially the same length.

The optical source is preferably an infra-red source but sources and sensors operating in other parts of the optical spectrum may be used in other embodiments.

A monitor in accordance with the invention may be used to detect vapour or gas concentration or may be used to provide other information depending on the regime under which it operates. However, typically, the gas monitor is used to determine concentration of a known gas by providing a comparison between the source intensity and intensity of optical radiation detected by the sensor after having been partially absorbed by the gas.

The reflective surfaces of the reflector means may be discontinuous in two or more discrete sections or present a continuous surface. In a preferred embodiment, the reflector means includes curved regions and planar regions to provide a compact arrangement. Preferably, the reflective surfaces are defined by interior surfaces of the chamber. The chamber may have polished walls or have a reflective coating laid down on it for example. The chamber may be fabricated by machining from a solid block of material, for example.

By employing the invention, radiation travelling from the source to the sensor over different routes can be arranged to travel along the same path length and hence the same amount of absorption occurs, giving an accurate measure of the concentration. In addition, as the optical paths are folded, this provides a particularly compact arrangement whilst giving relatively long optical paths through the gas. This makes a monitor in accordance with the invention convenient to use and include in other equipment. It also allows the monitor to be readily incorporated in a housing which can be made safe for use in hazardous environments where, for example, flammable or explosive gases are to be detected. Advantageously, for these applications, the housing is flameproof.

In a preferred embodiment of the invention, the source is arranged to heat substantially all the reflective surfaces, the folded configuration allowing this to be readily achieved. This reduces the risk of condensation on optical surfaces which in previously known devices has required a separate heater to be provided.

In a particularly advantageous embodiment of the invention, the reflective means includes a reflective surface or surfaces having part elliptical section to provide focusing of the optical radiation from the source and onto the sensor. The properties of an ellipse or ellipsoid are such that the optical path lengths along different routes between the source and sensor can be made substantially equal. In an advantageous embodiment of the invention, the source is located at a focus of a first ellipsoid and the sensor at a focus of a second ellipsoid, and the first and second ellipsoid having a common virtual focus. Preferably, the first and second ellipsoids have substantially the same dimensions. By employing this aspect of the invention, focusing of the optical radiation may also be achieved at a point intermediate the source and sensor along the optical path, enabling an accurate measurement of the concentration of the gas to be obtained. The reflective means may be thought of as comprising an ellipsoidal surface which is folded back on itself.

A planar reflective surface may form part of the optical path between the curved surfaces such as those which are part elliptical in section. The planar surface need not be located at the mid-point between the foci of either or both ellipses. If it is arranged nearer the source and reflector than the common virtual focus it results in a more compact arrangement than if it were arranged at the mid-point. In another embodiment of the invention, the reflector means includes offset parabolic surfaces to provide focusing at the source and sensor.

The source and sensor may be located exactly at foci of the reflector means or close to them. Similarly, although complete focusing of the optical radiation at the source and sensor will give more accurate measurements, it may be acceptable to provide a reduced amount of focusing in some circumstances.

The reflective means, source and sensor may be arranged such that there are only three reflections of light as it travels through the gas between the source and the sensor. In one particular advantageous embodiment however there are five reflections involved, giving long optical paths through the gas.

DESCRIPTION OF DRAWINGS

Some ways in which the invention may be performed are now described by way of example with reference to the accompanying drawings, in which.

DESCRIPTION OF PREFERRED EMBODIMENTS

Figure 1:
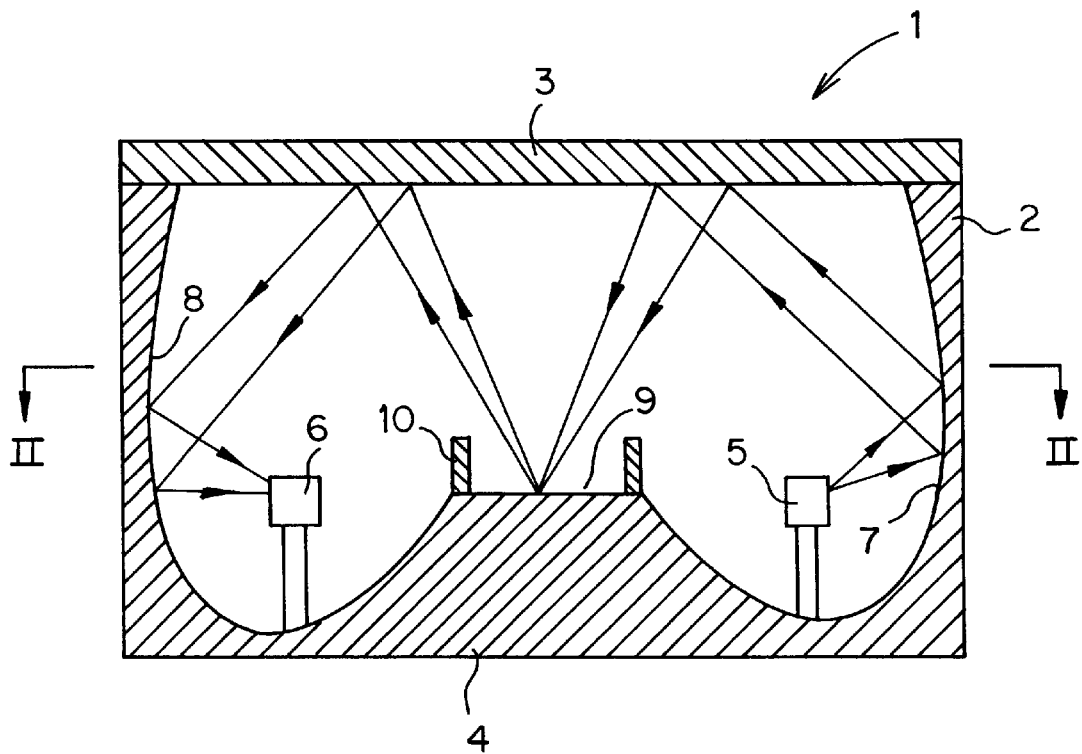
FIG. 1 is a transverse sectional schematic view of a gas monitor in accordance with the invention.
Figure 2:
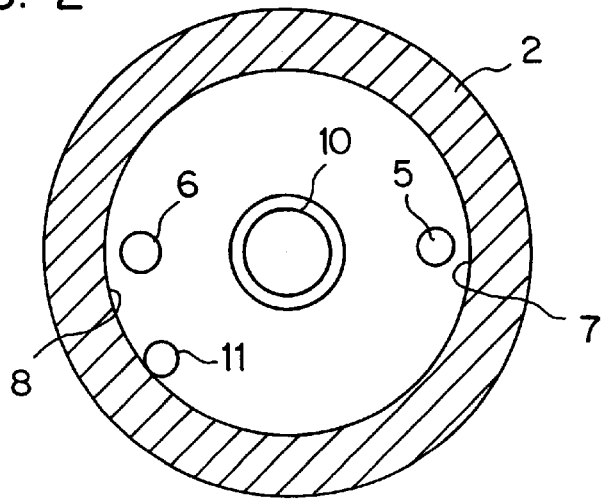
FIG. 2 is a view through II—II on FIG. 1.

With reference to FIGS. 1 and 2, a gas monitor 1 comprises a flameproof housing 2 having a cylindrical outer surface with end walls 3 and 4. The interior of the housing 2 contains an infra-red source 5 mounted on one of the end walls 4 and a pyroelectric detector 6 also mounted on the end wall 4. The interior surface of the housing 2 is of polished aluminium or some other material which reflects infra-red radiation.

The housing 2 defines a chamber within which gas to be monitored is contained. The chamber may be sealed following introduction of the gas but more usually includes an aperture or apertures (not shown) to allow gas to enter and leave the chamber from its surroundings.

The reflective curved wall 7 in the region of the source 5 is a part ellipse in section with the source 5 being placed at one of its foci. The wall 7 is curved in three dimensions to define a part-ellipsoid. The sensor 6 is located at a focus defined by the adjacent curved surface 8 which is also part elliptical in section, the reflective surfaces 7 and 8 being continuous and adjacent one another. The end wall 3 opposite that on which the source 5 and sensor 6 are mounted has a reflective inner surface which is planar. The wall 4 between the source 5 and sensor 6 has a reflective section 9 which is also planar and parallel to the end wall 3.

The configuration of the reflective surfaces and locations of the source 5 and sensor 6 are such that infra-red radiation emitted from the source 5 in most directions is directed onto the elliptical surface 7. Radiation reflected from the surface 7 is then incident on the planar surface 3 from which it is reflected and focussed on the region 9 between the source 5 and sensor 6. The radiation is then directed onto the elliptical surface 8 via the surface 3 to the detector 6, where it is focussed. Thus the radiation undergoes five reflections before being received at the sensor 6. A wall 10 surrounding the central region 9 reduces the amount of radiation which reaches the sensor 6 directly, without reflection, from the source or via a route other than that described above.

The housing also includes a reference sensor 11 which is located adjacent to the sensor 6 and used to compensate for changes in operating conditions and with time. Electrical connections to the source 5 and sensors 6 and 11 have been omitted from the Figure. There is an opening (not shown) in the planar surface 3 through which gas to be detected enters the chamber. Although not shown in the embodiment of FIG. 1, shielding additional to the wall 10 may be used to further reduce the amount of radiation travelling along paths other than that taken when reflected off the ellipsoidal surfaces.

Figure 3:
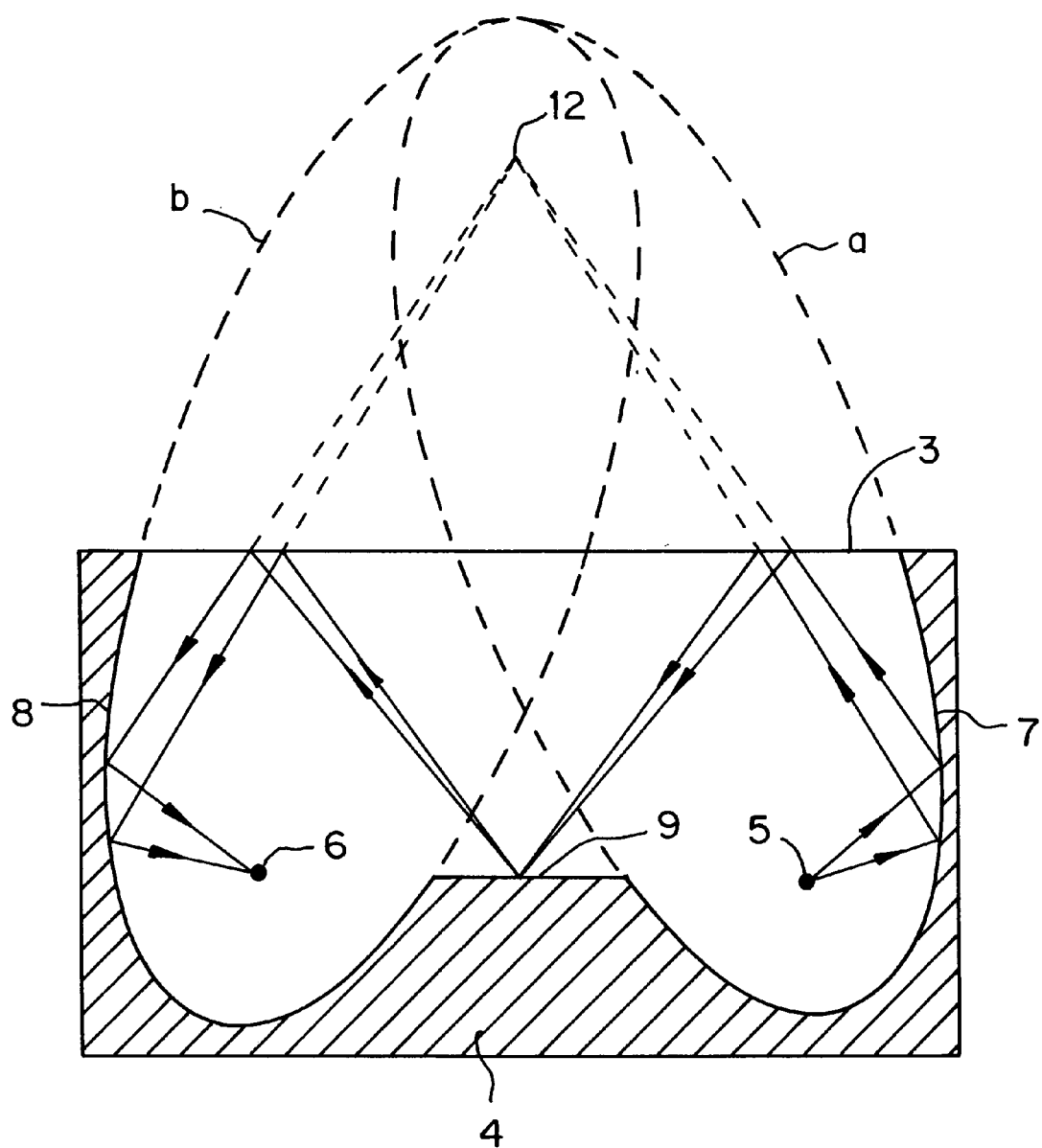
FIG. 3 is an explanatory schematic diagram relating to the gas monitor of FIG. 1.

FIG. 3 is an explanatory diagram in section illustrating the equality of optical path length for light emitted in different directions achievable by employing the invention. The parts of the housing are indicated schematically, with the end walls 3 and 4 being shown. The part ellipsoidal reflective surfaces 7 and 8 are shown as an unbroken line, the broken line illustrating the form of these surfaces if they were to be continued to form complete ellipsoids. The source 5 is located at a focus of an ellipse a which has a second focus 12, which in this case is a virtual focus as the elliptical surface does not continue beyond end wall 3. It is a property of an ellipse that light emitted from one focus is focussed at the second focus. The path of optical radiation from the source 5 is shown and, in the absence of the reflective surface 3 and assuming that the ellipse a were continuous, would be focussed at the second focus 12. Because of the intervening planar reflective surface 3, the light is instead focussed at the region 9 which is the same distance along the optical path from the source 5 as the virtual focus 12, region 9 being the same distance from the reflective surface 3 as the second focus 12.

The sensor 6 is located at a focus of an ellipse b which in this case, and preferably, has the same configuration as ellipse a and is orientated such that it has a virtual focus which coincides with virtual focus 12. Light reflected from the focussed region 9 is reflected from planar surface 3 and focussed by the ellipsoidal surface 8 onto the sensor 6. In the absence of the reflective surface 3 and if the ellipse b were complete, then this light would be reflected and focussed at the virtual focus 12. The properties of the ellipses ensure that light reflected from the source 5 in a plurality of different directions travels along the same path length before being refocussed at the sensor 6. The planar surface 3 may be located such that it is closer to the foci at which the source 5 and sensor 6 are positioned than it is to the virtual focus 12 to provide a more compact arrangement. This will require the reflective surface 9 to be re-positioned relative to the foci at 5 and 6 if it is still wished to obtain focusing of the light at this surface.

Although the above explanation given with reference to FIG. 3 is in relation to a two-dimensional section through the ellipsoidal surfaces, the reflective surfaces are three-dimensional and similar considerations apply to other sections through them.

Figure 4:
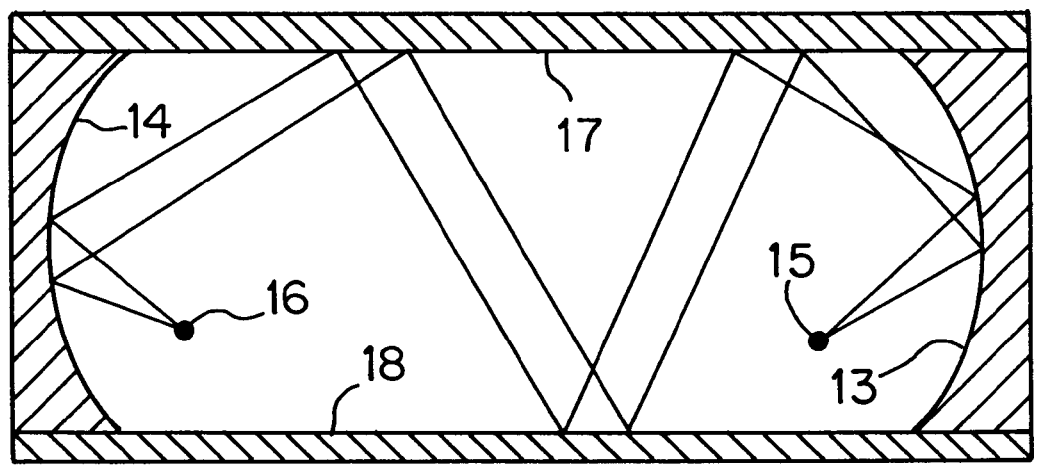
FIG. 4 illustrates schematically another gas monitor in accordance with the invention.

FIG. 4 illustrates schematically another gas monitor in which a chamber containing the gas has curved interior surfaces 13 and 14 which define foci at which an infra-red source 15 and sensor 16 are located. In this embodiment, the curved surfaces 13 and 14 are offset parabolas. Planar reflective surfaces 17 and 18 define part of the optical path between the source 15 and sensor 16. As the curved surfaces 13 and 14 are offset parabolas, there is no focussing of the infra red radiation at the reflective planar surface 18 located on a common substrate with the source 15 and sensor 16, but optical path lengths between the source 15 and sensor 16 are substantially equal for a wide angular spread of emitted radiation.

Although the above described embodiments each involve light being reflected five times as it travels between the source and sensor, in other examples only three or four reflections are involved. For example, instead of having three reflections from planar surfaces between two curved surfaces, only one reflection occurs at a planar surface. This may be achieved in an off axis parabola arrangement by one parabolic reflective surface being approximately normal to another such surface. In another device, the monitor illustrated in FIG. 1 might be modified by replacing planar region 9 with a part ellipsoidal surface having the sensor at it foucs. Light is then reflected three times as it passes through the gas. Other arrangements may involve more than five reflections.

We claim:

1. A gas monitor comprising: an optical source; a sensor sensitive to light from said source; a chamber containing gas to be monitored; and reflector means having reflective surfaces in said chamber and having foci; said source and sensor being located within said chamber and being substantially at said foci and light from the source being reflected at least three times at said reflective surfaces before reaching said sensor.

2. A monitor as claimed in claim 1 wherein said reflector means comprises curved surfaces defining said foci at which said source and sensor are located and a planar reflective surface.

3. A monitor as claimed in claim 2 wherein light from said source undergoes a first reflection at a curved surface, then three reflections at planar surfaces followed by a reflection at a curved surface.

4. A monitor as claimed in claim 1 wherein said source and sensor are mounted on a common wall of said chamber.

5. A monitor as claimed in claim 1 wherein said reflector means substantially defines a third focus between said foci.

6. A monitor as claimed in claim 1 wherein said reflective surfaces include at least one surface having a part elliptical section.

7. A monitor as claimed in claim 6 wherein said source is at a focus of a first part ellipsoidal surface and said sensor is at a focus of a second part ellipsoidal surface and said first and second ellipsoids share a common virtual focus.

8. A monitor as claimed in claim 7 wherein said first and second ellipsoids have substantially the same dimensions.

9. A monitor as claimed in claim 1 wherein said reflector means includes two off axis parabolas.

10. A gas monitor as claimed in claim 1 wherein said source and sensor are contained within a flameproof housing.

11. A monitor as claimed in claim 1 and including an optical shield to reduce the amount of light reaching said sensor from said source via routes other those which are desired.

12. A monitor as claimed in claim 1 wherein said source is arranged to heat substantially all said reflective surfaces to a temperature above ambient temperature.

13. A monitor as claimed in claim 1 wherein said optical source is an infra-red source.

14. A monitor as claimed in claim 1 wherein said reflective surfaces are defined by interior surfaces of said chamber.

* * * * *